United States Patent
Tsutsui et al.

(10) Patent No.: US 9,255,908 B2
(45) Date of Patent: Feb. 9, 2016

(54) TIGHTNESS MEASURING APPARATUS AND MEASURING METHOD

(71) Applicant: Hitachi, Ltd., Tokyo (JP)

(72) Inventors: Yoshitaka Tsutsui, Yokohama (JP); Nobuaki Nakasu, Kawasaki (JP); Harumasa Tsuchiya, Hitachi (JP); Keiji Suzuki, Hitachi (JP); Mitsuru Onoda, Takahagi (JP); Yasuaki Kageyama, Hitachi (JP)

(73) Assignee: Mitsubishi Hitachi Power Systems, Ltd., Yokohama (JP)

( * ) Notice: Subject to any disclaimer, the term of this patent is extended or adjusted under 35 U.S.C. 154(b) by 398 days.

(21) Appl. No.: 13/708,301

(22) Filed: Dec. 7, 2012

(65) Prior Publication Data

US 2014/0020470 A1 Jan. 23, 2014

(30) Foreign Application Priority Data

Jan. 11, 2012 (JP) ................................ 2012-002694

(51) Int. Cl.
*G01N 29/04* (2006.01)
*H02K 15/00* (2006.01)

(52) U.S. Cl.
CPC .......... *G01N 29/045* (2013.01); *H02K 15/0018* (2013.01)

(58) Field of Classification Search
CPC .......................... G01N 19/045; G01N 29/045
USPC ......................................... 73/12.09, 572, 579
See application file for complete search history.

(56) References Cited

U.S. PATENT DOCUMENTS

| | | | | | |
|---|---|---|---|---|---|
| 4,519,245 | A | * | 5/1985 | Evans | 73/579 |
| 4,889,000 | A | * | 12/1989 | Jaafar et al. | 73/865.8 |
| 6,631,335 | B2 | * | 10/2003 | Lusted et al. | 702/56 |
| 7,854,167 | B2 | * | 12/2010 | Hashiba et al. | 73/572 |
| 2009/0243419 | A1 | | 10/2009 | Humphries et al. | |

FOREIGN PATENT DOCUMENTS

| | | |
|---|---|---|
| JP | 02-080950 A | 3/1990 |
| JP | 03-082951 A | 4/1991 |
| JP | 2000-131196 | 5/2000 |
| JP | 2007-304057 A | 11/2007 |

OTHER PUBLICATIONS

Canadian Intellectual Property Office action on application 2,795,697 dated Jan. 15, 2014; pp. 1-3.

* cited by examiner

*Primary Examiner* — John Chapman, Jr.
(74) *Attorney, Agent, or Firm* — Foley & Lardner LLP

(57) ABSTRACT

According to a method by a frequency analysis of tap tones at the time when a tightness of a ripple member fixed by an elastic force has been tapped by a hammer or a method of detecting a response at the time when the ripple member has been vibrated, an enough precision cannot be obtained for a tightness estimation. A tapping force is applied to a plurality of positions on the member surface, thereby allowing a plurality of tap tones to be generated. Feature amounts are obtained from the plurality of tap tones. An average feature amount is obtained by averaging the feature amounts. The tightness of the ripple member is estimated from the average feature amount by using a correlation between the tightness of the ripple member and the average feature amount.

19 Claims, 12 Drawing Sheets

TIGHTNESS MEASURING APPARATUS AND MEASURING METHOD

INCORPORATION BY REFERENCE

The present application claims priority from Japanese application JP2012-002694 filed on Jan. 11, 2012, the content of which is hereby incorporated by reference into this application.

BACKGROUND OF THE INVENTION

The invention relates to a measuring technique of a wedge tightness which is used to fix a stator coil in a stator of a generator or the like.

A generator is constructed by a rotor and a stator and converts a change in magnetic field generated by a rotation of the rotor into an electric energy by the stator. The stator has such a structure that a coil is inserted into a slot of a core laminated with a silicon steel plate and is fixed with a pressure by an insulative member. As a pressure fixing method, the stator has such a structure that a ripple spring and a wedge serving as a plate-shaped member are overlaid over the coil and has such a structure that while compressing the ripple spring, it is pressed by the wedge, thereby fixing a coil conductor. In the generator having such a structure, it is necessary to maintain and manage the coil so as to be in a predetermined pressure fixing state. In the generator having such a coil fixing structure, after the elapse of predetermined years and months of use, the fixing state of the wedge is inspected and if there is looseness, an exchange and a maintenance of the ripple spring and the wedge are performed in order to recover a pressing force. Hitherto, an inspection and a discrimination of the coil fixing state have been performed by a person in dependence on such a sensory test that he applies a tap to the wedge by using a hammer for inspection and discriminates the coil fixing state on the basis of a tone and a vibration which are generated at this time. As a trial for realizing such a sensory test by an apparatus, there is a technique disclosed in JP-A-2000-131196. According to such a technique, a peak value in each frequency band of the tone which is generated by the hammer tap to the wedge is obtained and is compared with a preset reference value, thereby discriminating a looseness state.

SUMMARY OF THE INVENTION

In the case where the tightness of the wedge is discriminated by a person, a variation due to a discrimination result occurs by a degree of an experience and skill, a feeling, a physical condition, and the like of the person who measures. A report by JP-A-2000-131196 shows that a frequency of a tap tone has a relation with the looseness state of the wedge. However, since the tap tone frequency changes in dependence on a tapping force, a sufficient precision cannot be obtained in quantization of the wedge fixing state.

According to an aspect of the invention, the invention includes a plurality of means for solving the above problems and, according to one example of the present invention, a plurality of tap tones are generated by applying a tapping force to a plurality of positions on the surface of a member, a first feature amount is obtained from the plurality of tap tones, a second feature amount is obtained from the first feature amount, a tightness of the member is obtained by using a correlation between the tightness of the member and the second feature amount.

According to the invention, since the tightness of the wedge of the generator stator can be quantized, a reliability of a wedge assembling operation in an assembly of the generator stator can be raised.

In the generator which is being used, by periodically measuring the wedge tightness by a periodic inspection or the like, an aging change of the wedge tightness (coil tightness) can be grasped. By accumulating such data, timing for exchanging the stator wedge can be estimated and the maintenance of the generator can be efficiently performed. Thus, the costs, energy, and the like which are required for the maintenance can be reduced.

Other objects, features and advantages of the invention will become apparent from the following description of the embodiments of the invention taken in conjunction with the accompanying drawings.

DESCRIPTION OF THE EMBODIMENTS

Embodiments will be described hereinbelow with reference to the drawings.

Embodiment 1

Figure 1:
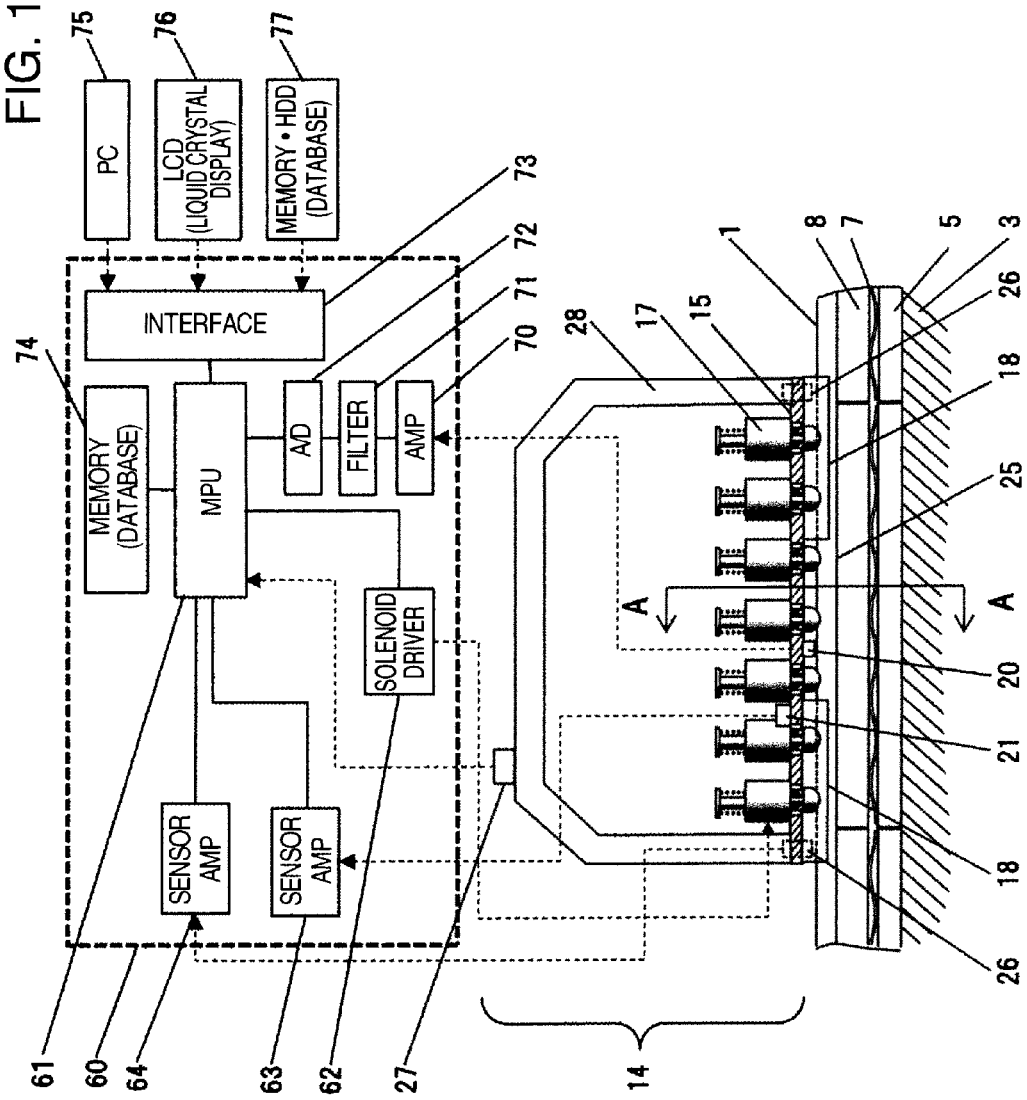
FIG. 1 is a schematic diagram showing a construction of an embodiment 1.
Figure 2A:
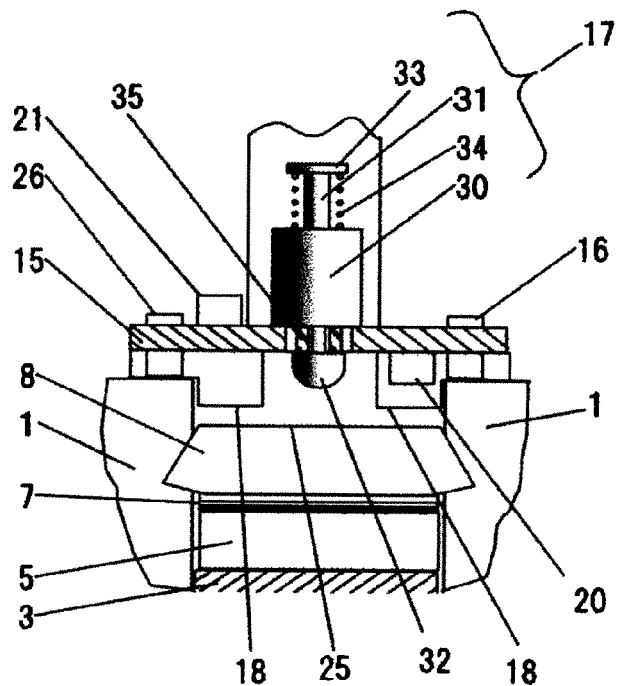
FIGS. 2A and 2B are diagrams taken along the line A-A in FIG. 1.
Figure 2B:
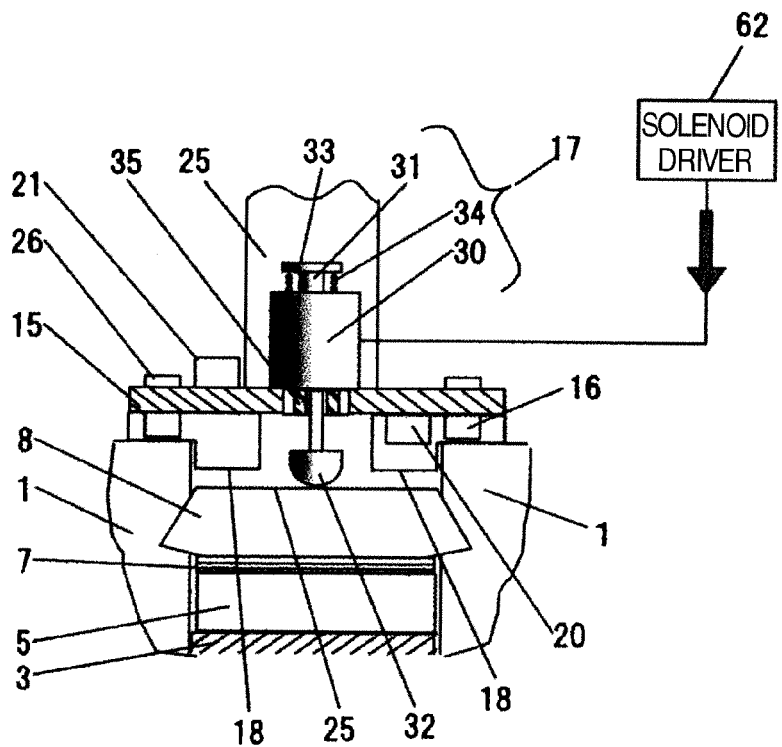
Figure 3:
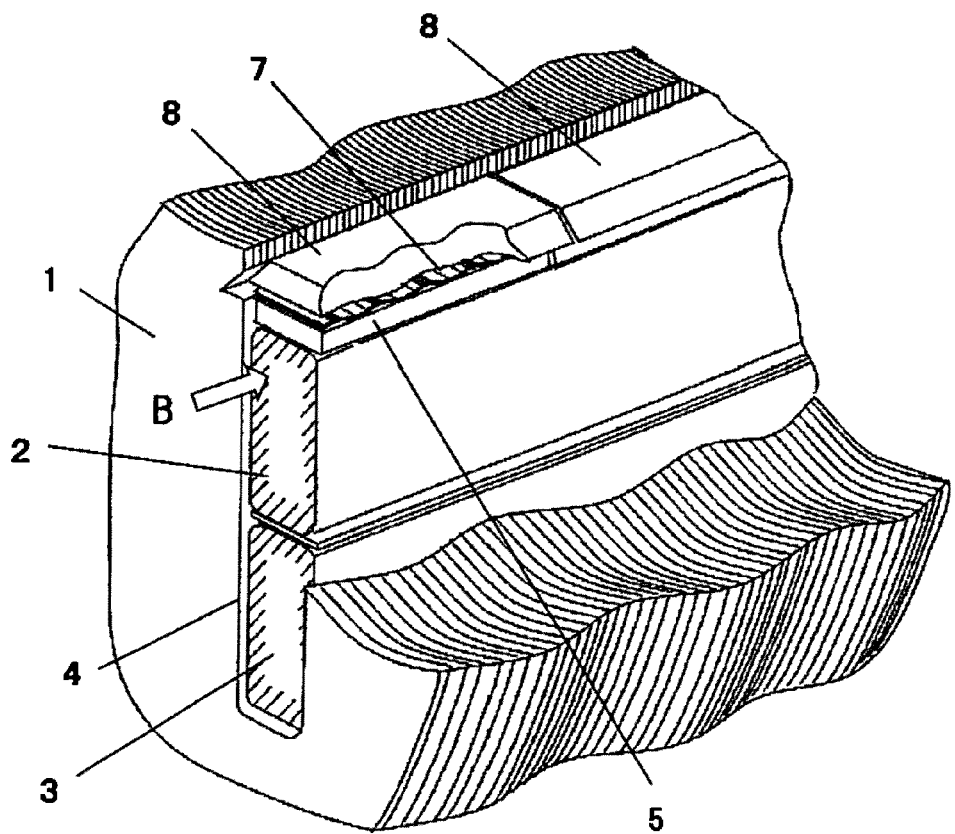
FIG. 3 is a partial cross sectional view of a generator stator serving as a measurement target product.
Figure 4:
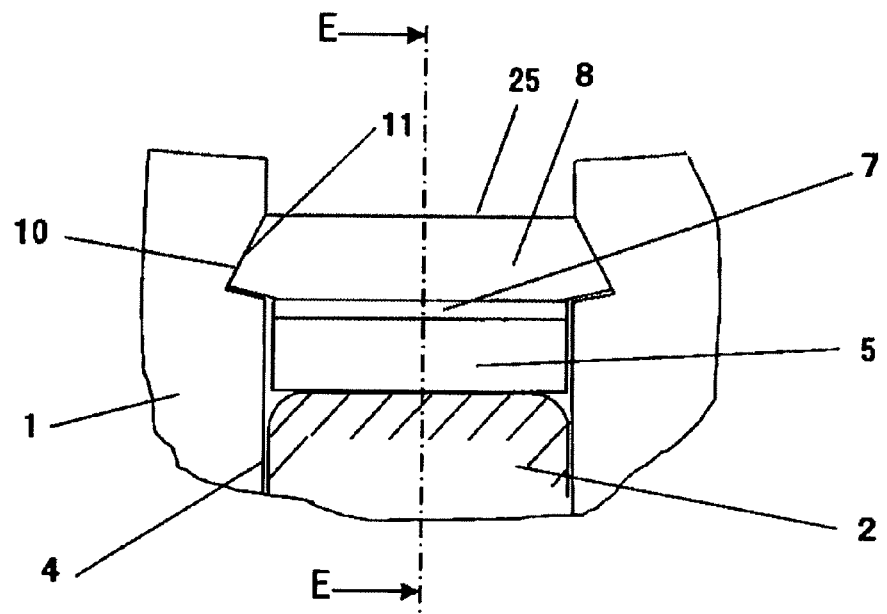
FIG. 4 is a partial enlarged diagram of FIG. 3.

FIGS. 1, 2A, and 2B show an example of a construction of a wedge tightness measuring apparatus of an embodiment. FIGS. 2A and 2B are diagrams taken along the line A-A in FIG. 1. FIG. 3 is a partial cross sectional view showing a structure of a measurement target. FIG. 4 is a diagram (front view) taken along an arrow B in FIG. 3.

First, the structure of the measurement target will be described with reference to FIGS. 3 and 4. FIG. 3 is a partial cross sectional view showing a part of a generator stator. The generator stator has a coil fixing structure as illustrated in the diagram in order to prevent such a situation that a coil is vibrated by an electromagnetic force generated in the coil by a current at the time of power generation. In FIG. 3, reference numeral 1 denotes a core laminated with a silicon steel plate, 4 indicates a groove formed in the core 1, and 2 and 3 denote coils inserted in the groove 4. A plate 5, a ripple spring 7, and a wedge 8 are laminated on the coil 2 and their materials are a composite material in which a resin having high insulation performance has been impregnated and hardened.

In FIG. 4, the wedge 8 is inserted so that a notched groove 10 formed in the groove 4 of the core 1 and a taper portion 11 of the wedge 8 come into contact with each other. In this structure, the ripple spring 7 is in a compression state. The coils 2 and 3 are pressed by a force generated by the compressed ripple spring 7 and its reaction force is applied to the wedge 8. Further, the force applied to the wedge 8 is received by the notched groove 10 of the groove 4 formed in the core 1 into which the wedge 8 has been fitted. In the coil fixing structure illustrated in FIG. 3, since it is difficult to directly measure the fixing state of the coils 2 and 3, the fixing state of the wedge 8 to which the equivalent reaction force has been applied is measured.

Subsequently, the wedge tightness measuring apparatus shown in FIG. 1 be described.

In FIG. 1, reference numeral 14 denotes a measuring probe in the wedge tightness measuring apparatus. In the measuring probe 14, reference numeral 15 denotes a base plate and 17 indicates a tapping mechanism fixed to the base plate 15. In the embodiment, seven tapping mechanisms 17 have been fixed at a regular pitch. Reference numeral 18 denotes guide blocks fixed to the base plate 15. The guide blocks 18 are fitted into the groove 4 of the core 1 as illustrated in FIG. 2A, thereby deciding positions in the right and left directions of the measuring probe 14 in the diagram.

Reference numeral 20 denotes a microphone for collecting a tap tone generated when a wedge surface 25 has been tapped by the tapping mechanism 17. Reference numeral 21 denotes an acceleration sensor fixed to the base plate 15. The acceleration sensor 21 detects a direction in which a gravity acts on the measuring probe 14, thereby detecting a posture of the measuring probe. Reference numeral 28 denotes a handle fixed to the base plate 15. In the embodiment, a person grasps the handle 28 and measures while depressing the measuring probe 14 to the core 1. Reference numeral 26 denotes core detecting sensors fixed at four corners of the base plate 15. The detecting sensors 26 detect that the probe 14 has been depressed to the core 1. As such a sensor, a reflection type photoelectric sensor, a proximity sensor using an electromagnetic induction, a small micro switch, or the like can be used. Reference numeral 27 denotes a push-button switch to start the measurement.

The tapping mechanism 17 will now be described with reference to FIGS. 2A and 2B. In the tapping mechanism 17, reference numeral 30 denotes a solenoid actuator of a direct-acting type and its internal axis 31 is vertically driven by ON/OFF of a current. A hammer 32 is fixed to a lower edge of the axis 31 and a collar 33 is fixed to the other edge. In a state where no current is supplied to the solenoid 30, a spring 34 acts so as to keep the hammer 32 at an ascending position (state shown in FIG. 2A). A cushioning material 35 has been inserted between the solenoid 30 and the hammer 32. The cushioning material 35 absorbs an impact generated when the hammer 32 ascends and collides with the solenoid 30, thereby suppressing the generation of the tone. As for the operation of the tapping mechanism 17, when the solenoid 30 is energized, the hammer 32 descends as illustrated in FIG. 2B and taps the surface 25 of the wedge 8, so that a tap tone is generated. When the energization to the solenoid 30 is stopped, the hammer ascends by the operation of the spring 34 and is returned to the state of FIG. 2A.

In the wedge tightness measuring apparatus shown in FIG. 1, tapping control of the wedge 8 by the measuring probe 14 and a processing unit 60 for calculating tightness from the wedge tap tone will now be described. Reference numeral 61 denotes a microprocessor unit (hereinbelow, abbreviated to MPU). The MPU 61 controls the seven tapping mechanisms 17 in accordance with signals from the sensors 21 and 26, the switch 27, and the like, processes a tone signal from the microphone 20, and executes an arithmetic operation in accordance with an internal program as will be explained hereinafter, thereby estimating the wedge tightness. Reference numeral 62 denotes a solenoid driver for supplying a current to the solenoid 30 on the basis of a signal from the MPU 61 and driving it. The MPU 61 can independently control the solenoids 30 of the seven tapping mechanisms 17.

Reference numeral 63 denotes a sensor amplifier for amplifying or converting the signal from the acceleration sensor 21 and transferring to the MPU 61. Reference numeral 64 denotes a sensor amplifier for independently transferring the signals from the four core detecting sensors 26 to the MPU 61. The switch 27 is connected to MPU 61 and generates a measurement start signal. Reference numeral 70 denotes an amplifier for amplifying a sound signal from the microphone 20, 71 indicates a filter for eliminating unnecessary frequency components from the signal amplified by the amplifier 70, and 72 denotes an A/D converter for converting the analog signal processed by the filter into a digital signal so as to be processed by the MPU 61. Reference numeral 74 denotes a memory for storing data. The memory 74 stores a result obtained by arithmetically operating the digital signal from the A/D converter 72 by the MPU 61, a database which is referred to in order to estimate the wedge tightness, and the like. Reference numeral 73 denotes an interface for connecting the MPU 61 to an external personal computer 75, an LCD (liquid crystal display) 76, an external memory 77, and the like.

Figure 5:
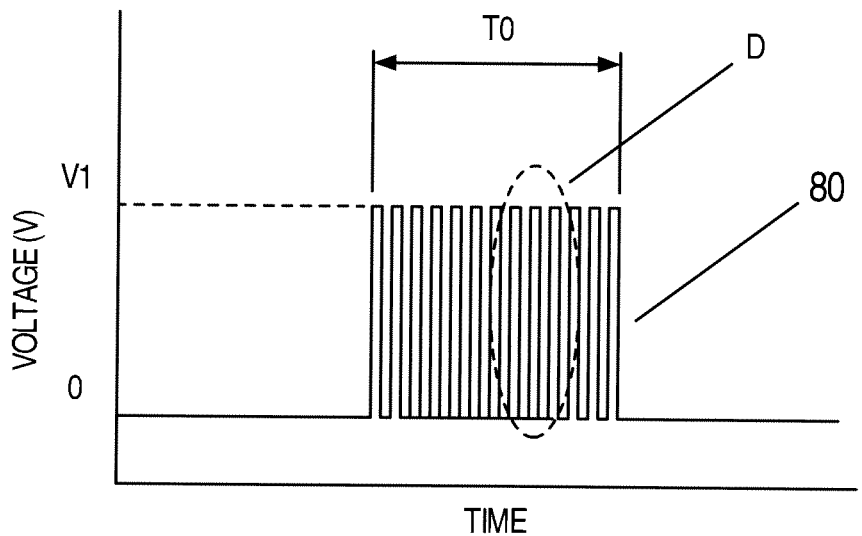
FIG. 5 is a voltage waveform diagram for a solenoid control system.
Figure 6:
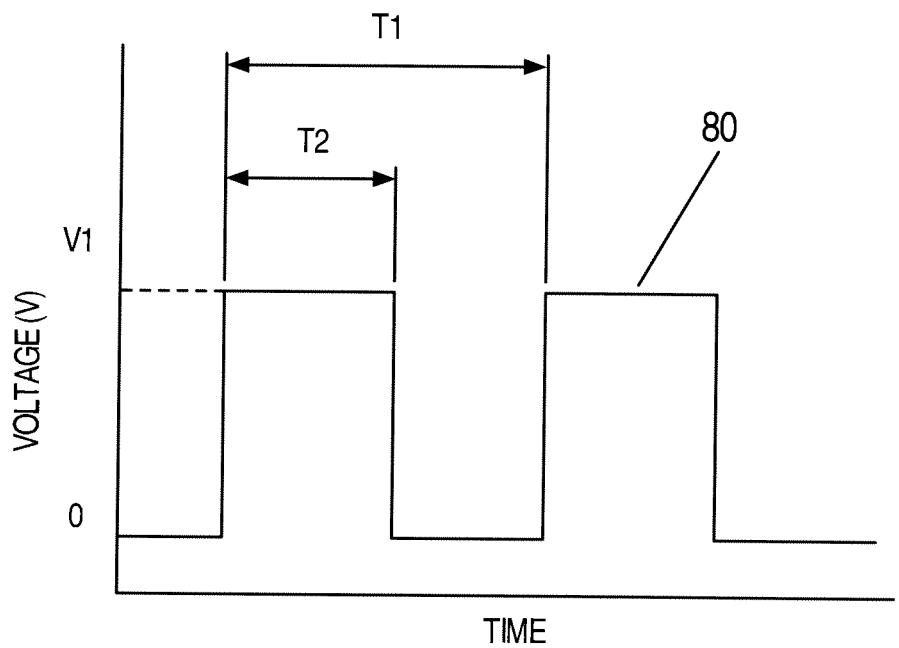
FIG. 6 is an enlarged diagram of FIG. 5.

A tapping force control method of the tapping mechanism 17 will now be described with reference to FIGS. 2A, 2B, 5, and 6. As for the tapping operation by the tapping mechanism 17, as shown in FIG. 2B, by supplying a current from the solenoid driver 62 to the solenoid 30, the axis 31 is descended, thereby allowing the tip hammer 32 to collide with the wedge 8. At this time, a tapping force of the hammer 32 to the wedge 8 is proportional to an electric power which is applied to the solenoid 30. In the embodiment, the driving current to the solenoid 30 is controlled by a PWM (Pulse Width Modulation) system. A driving voltage waveform 80 is shown in FIG. 5. By applying a driving voltage V1 to the solenoid 30 for a predetermined time (T0), the hammer 32 is vertically moved for a short time of about 100 msec, thereby applying a tap to the wedge. An enlarged diagram (D portion enlargement) of the driving voltage waveform 80 at this time is shown in FIG. 6. The driving voltage waveform 80 has a pulse-like shape of the voltage V1 and it is assumed that a period of pulses is equal to T1 and a time when the voltage is at the high level is equal to T2. T2/T1 as a ratio of a generation time of the voltage to the period of pulses is controlled. Since an electric power of the control signal from the MPU 61 is generally small the solenoid driver 62 is constructed by using a power transistor or the like and the signal from the MPU 61 is amplified, thereby forming the driving voltage waveform 80. The tapping force is proportional to a current supplying time T2 and becomes maximum when T2=T1.

Figure 7:
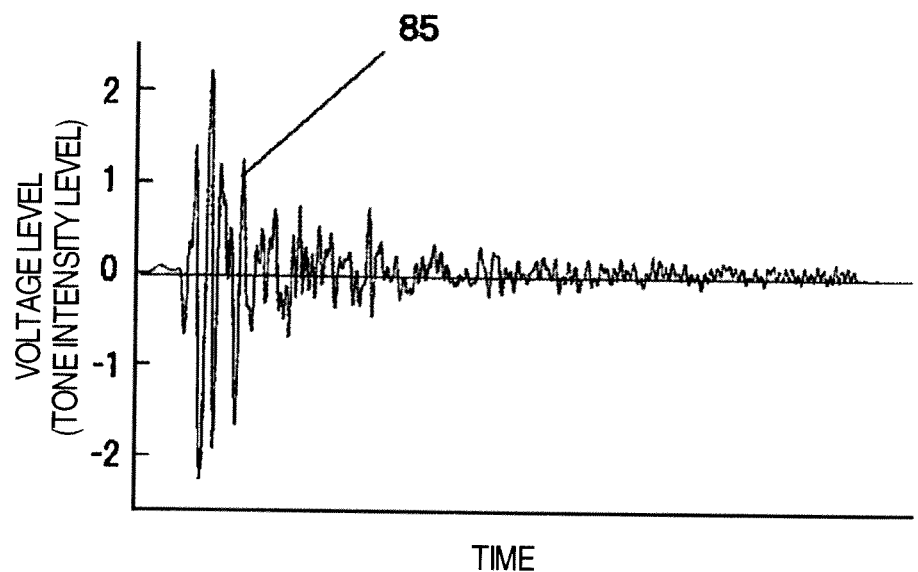
FIG. 7 is a waveform diagram of a tap tone signal.
Figure 8:
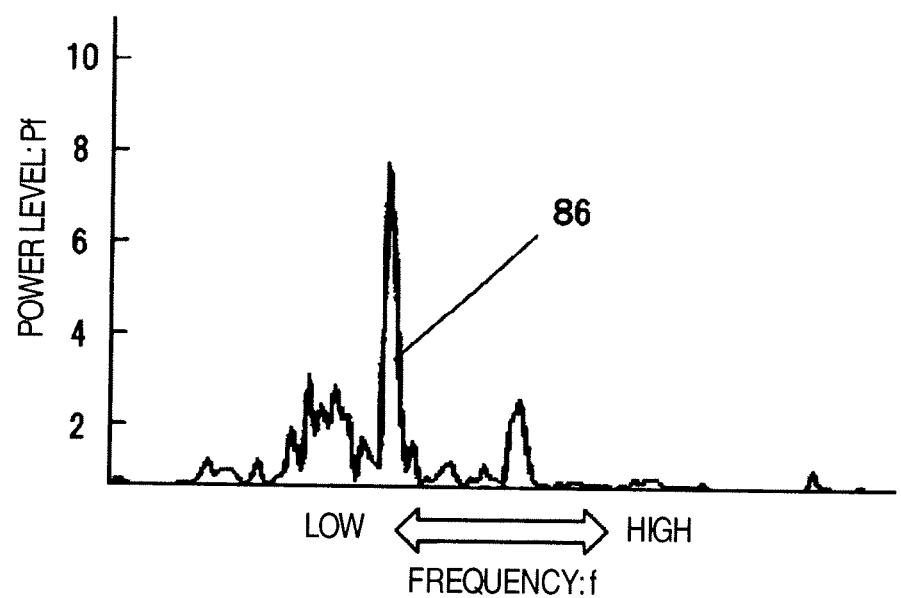
FIG. 8 is a power spectrum diagram of the tap tone signal.

Subsequently, a signal processing method of estimating the wedge tightness from the tap tone will be described. A conversion result 85 of the wedge tap tone obtained by the A/D converter 72 is shown in FIG. 7. This conversion result is obtained by converting an intensity level of a tone to time into a digital voltage signal level. FIG. 8 shows a power spectrum 86 obtained by FFT (Fast Fourier Transform) processing the signal in FIG. 7 and shows a relation between a frequency and a power level of the tone.

The estimating method of the wedge tightness will be described with reference to FIGS. 9 to 13. With respect to the power spectrum 86 of the tap tone generated by tapping the wedge, the power level at each frequency f is assumed to be Pf and a sum Ps of the power levels at the respective frequencies (hereinbelow, referred to as a total power level) is obtained by the following equation (1).

$$Ps = \Sigma Pf \qquad (1)$$

An experiment result in which the wedge tightness is used as a factor and a relation between the tapping position of the wedge and the total power level Ps has been obtained will now be described.

Figure 9:
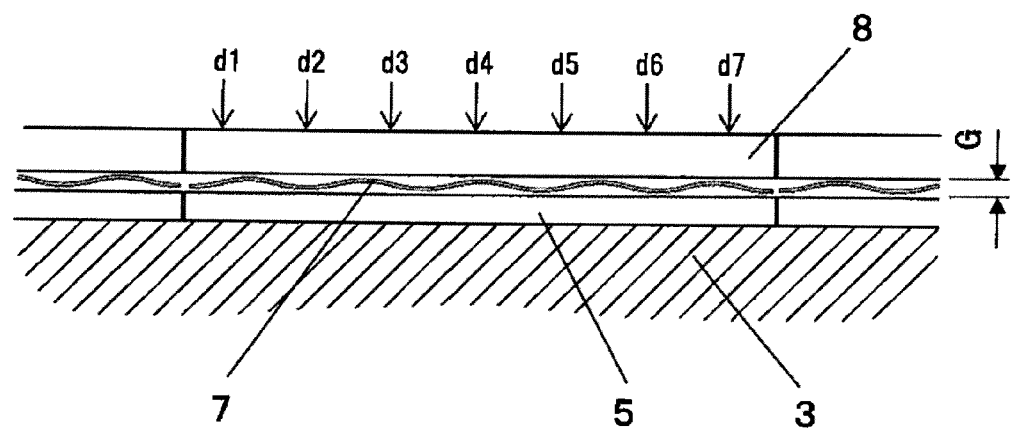
FIG. 9 is an explanatory diagram of wedge tapping positions.

The tapping positions are shown by d1 to d7 in FIG. 9 and correspond to the diagram taken along the line E-E in FIG. 4. The tightness is set by changing a compression amount (gap G in the diagram) of the ripple spring 7 to three stages of "large", "middle", and "small". In the diagram, d1 to d7 denote the tapping positions in the wedge 8. Intervals among them are set to a regular pitch. Center positions in the right/left direction of the wedge shown in FIG. 4 were tapped by the same force.

Figure 10:
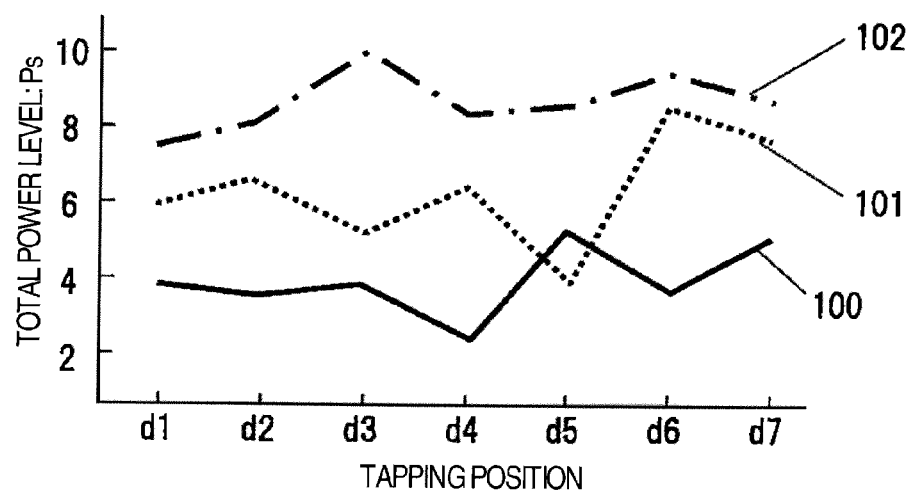
FIG. 10 is a graph showing a relation between the tapping position and a total power level.

FIG. 10 shows a relation between the tapping position and the total power level Ps, A curve 100 shows a result when the wedge tightness level is small, a curve 101 shows a result when the wedge tightness level is middle, and a curve 102 shows a result when the wedge tightness level is large, respectively.

There is such a tendency that the tightness and the total power level Ps are proportional. However, the total power level Ps of the tap tone fluctuates largely in dependence on the tapping position. According to this result, if samples are remade and experiments are performed, the positions of mountains and valleys fluctuate. As shown at the tapping position d5 in the curves 101 and 102, a case where the total power levels to the set tightness level are reversed also occurs. Therefore, if the tightness of the wedge 8 is estimated from the total power level of the tap result at one proper position of the wedge, a possibility that an estimation error increases is high.

Figure 11:
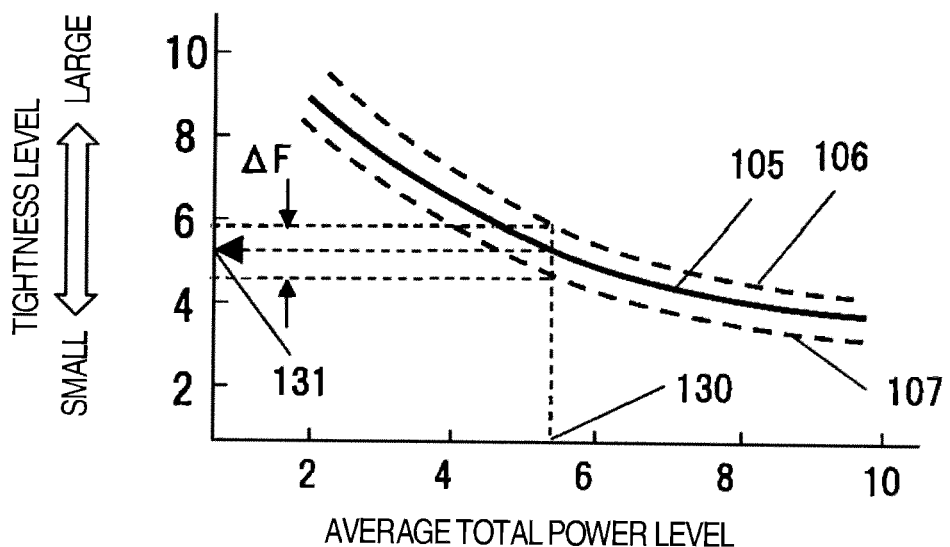
FIG. 11 is a graph showing a relation between a tightness level and an average total power level.
Figure 12:
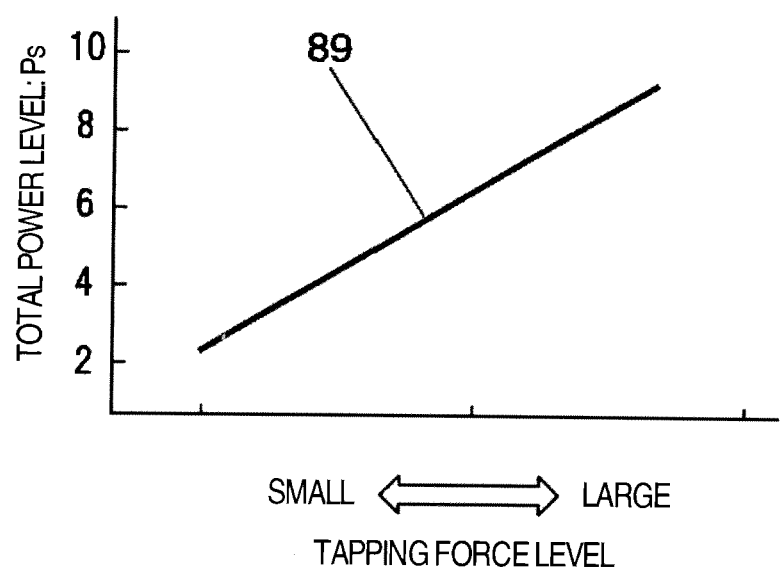
FIG. 12 is a graph showing a relation between a tapping force level and the total power level.

Therefore, in order to estimate the tightness by using a value of the total power level, an average value of the total power levels at seven positions of d1 to d7 of the graphs 100, 101, and 102 in FIG. 10 (hereinbelow, referred to as an average total power level) is set to a representative value of the total power level to one wedge. When a relation between the average total power level and the tightness level is obtained, a graph of FIG. 11 is obtained. In FIG. 11, a curve 105 indicates a relation between the tightness level and the average total power level obtained from a plurality of model samples. Each of curves 106 and 107 indicates a variation range among the plurality of samples. If such a graph is used, when a certain average total power level 130 is obtained, a tightness level estimation value 131 corresponding to the curve 105 can be obtained. At this time, an estimation range of the tightness level is equal to $\Delta f$ which is decided by the ranges of the curves 106 and 107. Since the estimation range $\Delta f$ can be reduced by increasing the number of averaging points, an estimation precision can be raised by increasing the number of tapping times to the same wedge.

By the above result, if a correlation between the tightness and the average total power level is preliminarily obtained as a database, the tightness level can be estimated from the measurement value of the average total power level by using the database.

It is an important point that the tapping force variation to obtain the total power level Ps at each tapping position is reduced. This is because since there is a proportional relation between the total power level Ps and the tapping force level as shown in a graph 89 in FIG. 12, the variation of the tapping force level exerts an influence on the total power level Ps.

Figure 13:
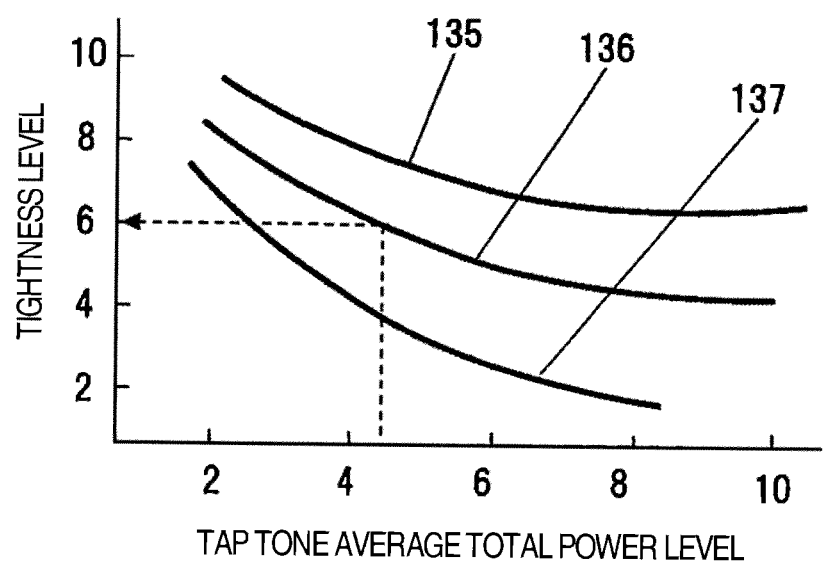
FIG. 13 is a graph showing a relation between the average total over level and the tightness level.

Since most of the large generators are produced to order, a design of the product differs in dependence on the customer. Therefore, a plurality of shapes, materials, and the like of the wedges as tapping targets exist. The relation between the tightness level and the average total power level also differs in dependence on the size and material of the wedge. Therefore, as shown in FIG. 13, as relations between the average total power levels and the tightness levels of various kinds of products, if a curve 135 of a product 1, a curve 136 of a product 2, a curve 137 of a product 3, and the like are preliminarily obtained as a database, it is possible to cope with the various kinds of products by estimating the wedge tightness level.

Further, in the case of coping with a wedge of a material and a shape which do not exist in the database, when physical properties and a shape of a new wedge are inputted, an approximate function to estimate a tightness corresponding to the new wedge is formed and estimated for the new wedge on the basis of the database of the wedge whose physical properties and shape are closest. Or, it is also possible to cope with such a wedge by a method whereby the wedge whose physical properties and shape are closest to those of the new wedge is provided to the operator, thereby allowing him to select it.

Although the total power level has been used as a feature amount to estimate the wedge tightness in the above method, the estimation can be performed by using any feature amount so long as it is a physical amount having a correlation with the wedge tightness. For example, the following method is considered: a method whereby an amplitude spectrum is used in place of the power spectrum and the sum of amplitude levels at respective frequencies in the amplitude spectrum is used as a feature amount, a method whereby an attenuation factor is obtained from a time of the tone and a vibration waveform of a tone intensity level in FIG. 7 and this attenuation factor is used as a feature amount; a method whereby in power spectrum distribution of the collected tap tones, a value of a frequency at which a sum value of the power levels at the respective frequencies is divided into the halves at the upper and lower frequency bands is used as a feature; a method whereby in amplitude spectrum distribution of the collected tap tones, a value of a frequency at which a sum value of the amplitude levels at the respective frequencies is divided into the halves at the upper and lower frequency bands is used as a feature; or the like.

Figure 14:
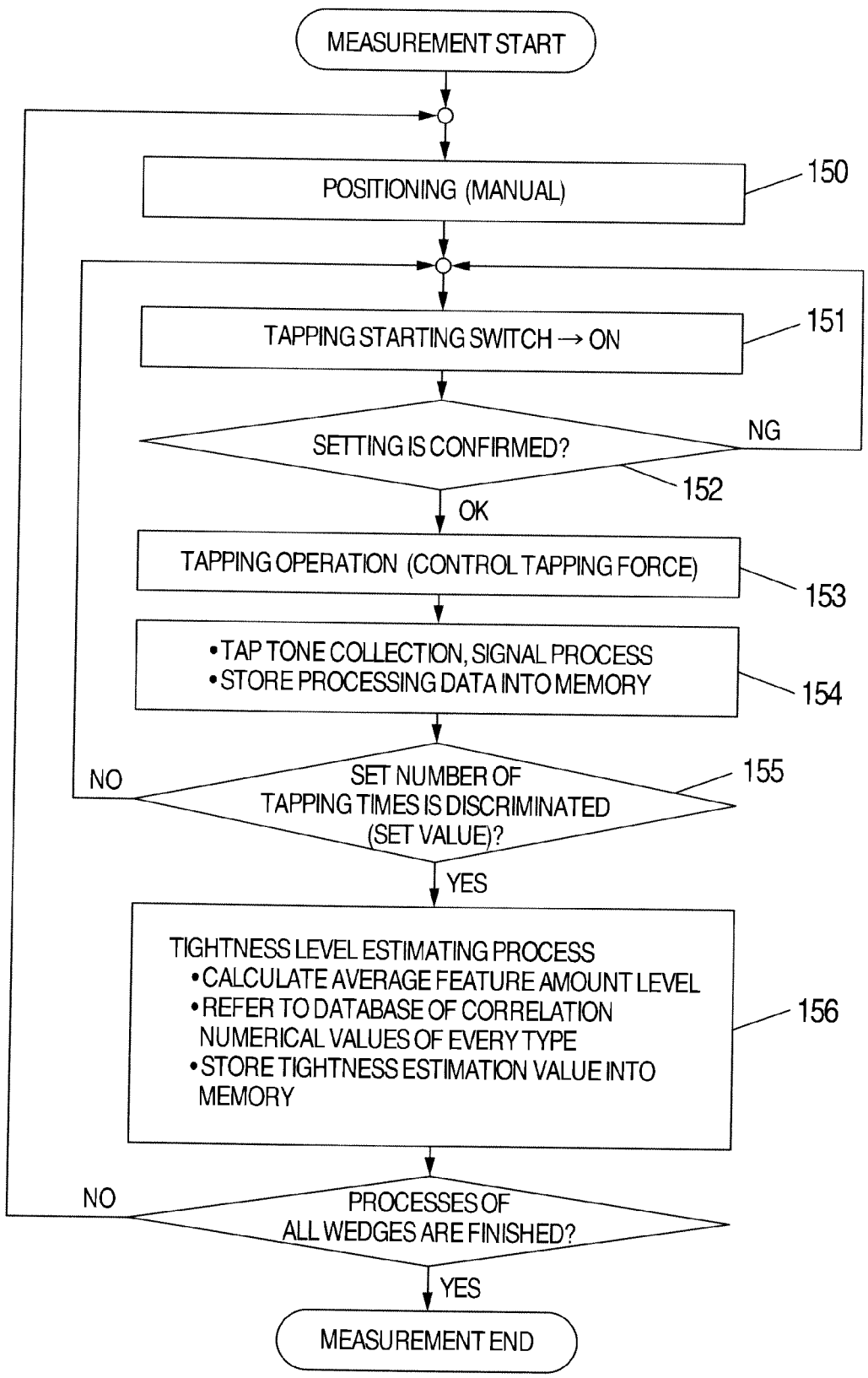
FIG. 14 is a flowchart showing the operation of the embodiment 1.

An operation flow of the tightness measuring apparatus shown in FIG. 1 is shown in FIG. 14. A tightness measuring method will be described hereinbelow with reference to the operation flow.

First, as a positioning operation 150, to a stator core having a wedge serving as a measurement target, the guide blocks 18 of the measuring probe 14 are inserted into the groove of the core and the position of the measuring probe 14 is decided.

Subsequently, the measurement starting switch 27 is turned on as a measurement starting operation 151. At this time, as a confirmation 152 of the setting of the measuring probe, if all of the core detecting sensors 26 fixed at the four corners are ON, it is determined that the measuring probe 14 has correctly been depressed to the core 1, and the measuring operation is started. The monitoring of the depression state by the core detecting sensors 26 is always performed during the measurement. If any one of the four core detecting sensors 26 is not ON, the measuring operation is not executed.

If the measuring probe 14 has correctly been depressed, a tapping operation 153 to the wedge 8 by the tapping mechanisms 17 is started. Since there are seven tapping mechanisms 17 in the embodiment, first, the wedge 8 is tapped by the tapping mechanism 17 existing at the left edge. At this time, the posture of the tightness measuring probe 14 is detected by the acceleration sensor 21 and the current which is supplied to the solenoid 30 for the gravity direction is controlled. Since the wedge as a measurement target is arranged in the circumferential direction of a cylinder, the tapping posture of the measurement target wedge changes and a gravity which is applied to a movable portion of the tapping mechanism 17 changes depending on the posture. Therefore, in order to keep the tapping force constant, it is necessary to detect the direction of the gravity and correct it. Thus, the constant tapping force can be applied to the wedge 8 irrespective of the posture position of the wedge 8.

Subsequently, a tap tone collection and a signal process 154 are executed. A value of the total power level Ps is obtained by the tap tone collection and the signal process of the wedge. As timing for fetching the tap tone by the microphone 20 into the MPU 61, the tapping start signal to the tapping mechanism 17 is used as a trigger and the tap tone is fetched for a time of about 10 to 100 msec. Thus, only the tap tone data necessary to estimate the tightness can be collected. The tap tone is transmitted through the amplifier 70 and the filter 71, is converted into digital data by the A/D converter 72, and is inputted to the MPU 61. The FFT (Fast Fourier Transform) process is executed to the digital signal by using an arithmetic operating function of the MPU 61, the power spectrum 86 shown in FIG. 8 is obtained. Further, the total power level Ps is obtained from the power spectrum 86 by the equation (1). Those data is stored into a proper memory area. In this manner, the tapping by the tapping mechanism 17 existing at the left edge and the tap tone data process are finished.

Since a plurality of positions of one wedge are tapped, the tap tone collection and the signal process are repeated the number of times which has been set in a judgment 155 of the number of tapping times. Since there are seven tapping mechanisms in the embodiment, by sequentially repeating the operation seven times, seven total power levels at the different positions can be obtained for one wedge 8. An average total power level is obtained from the seven total power levels and stored into a proper memory area. Subsequently, a tightness level estimating process 156 is executed. Upon estimation of the wedge tightness level, it is obtained by comparing and referring to the value of the average total power level stored in the memory 74 and the numerical value database showing the correlation between the wedge tightness level which has previously been formed every type of measurement target and the average total power level. The obtained tightness estimation value is stored in the memory 74. In this manner, the tightness estimation value to one wedge is obtained. Subsequently, by repeating a procedure similar to that mentioned above, tightness estimation values are obtained with respect to all wedges of the generator stator serving as a measurement target and the measurement is finished.

A person confirms the wedge tightness data recorded in the memory 74 by using the personal computer 75 and the display 76 such as an LCD connected to the processing unit 60 and stores them as data for management into the external memory 77.

According to the foregoing measuring method, since the wedge 8 is tapped by the tapping force which has properly been controlled, the variation in total power level of the tap tone that is caused by the variation in the tapping force can be reduced. Since the tightness of the wedge is estimated for one wedge on the basis of the average value of the total power levels obtained from the predetermined positions by the plurality of tapping mechanisms 17, the tightness estimation error that is caused by the variation in the total power level due to the tapping positions in the wedge can be suppressed. Therefore, the tightness can be estimated from the wedge tap tone. Consequently, the quantization of the wedge tightness which has been performed by a person in dependence on the sensory test so far can be realized.

Embodiment 2

Figure 15:
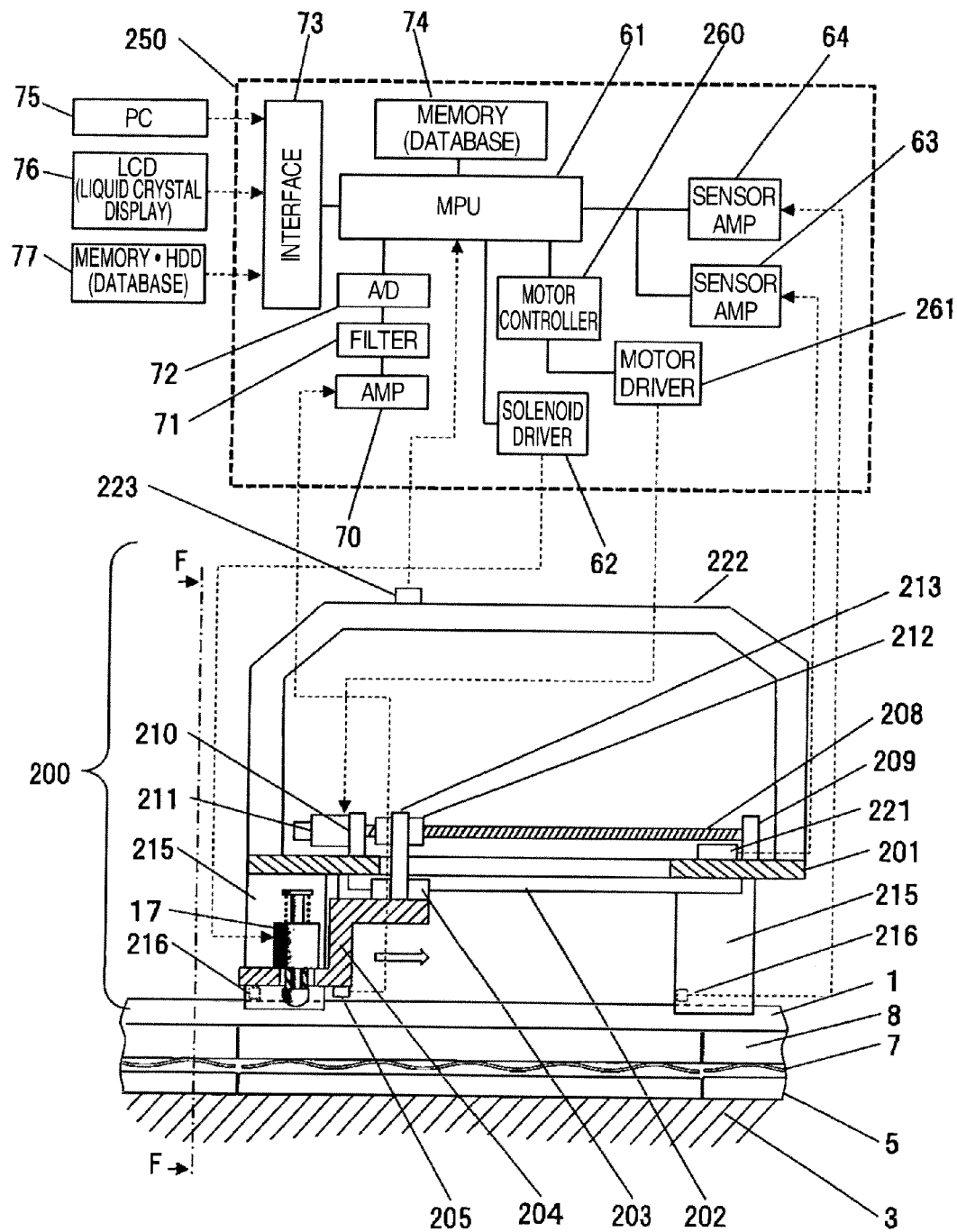
FIG. 15 is a schematic diagram showing a construction of an embodiment 2.
Figure 16:
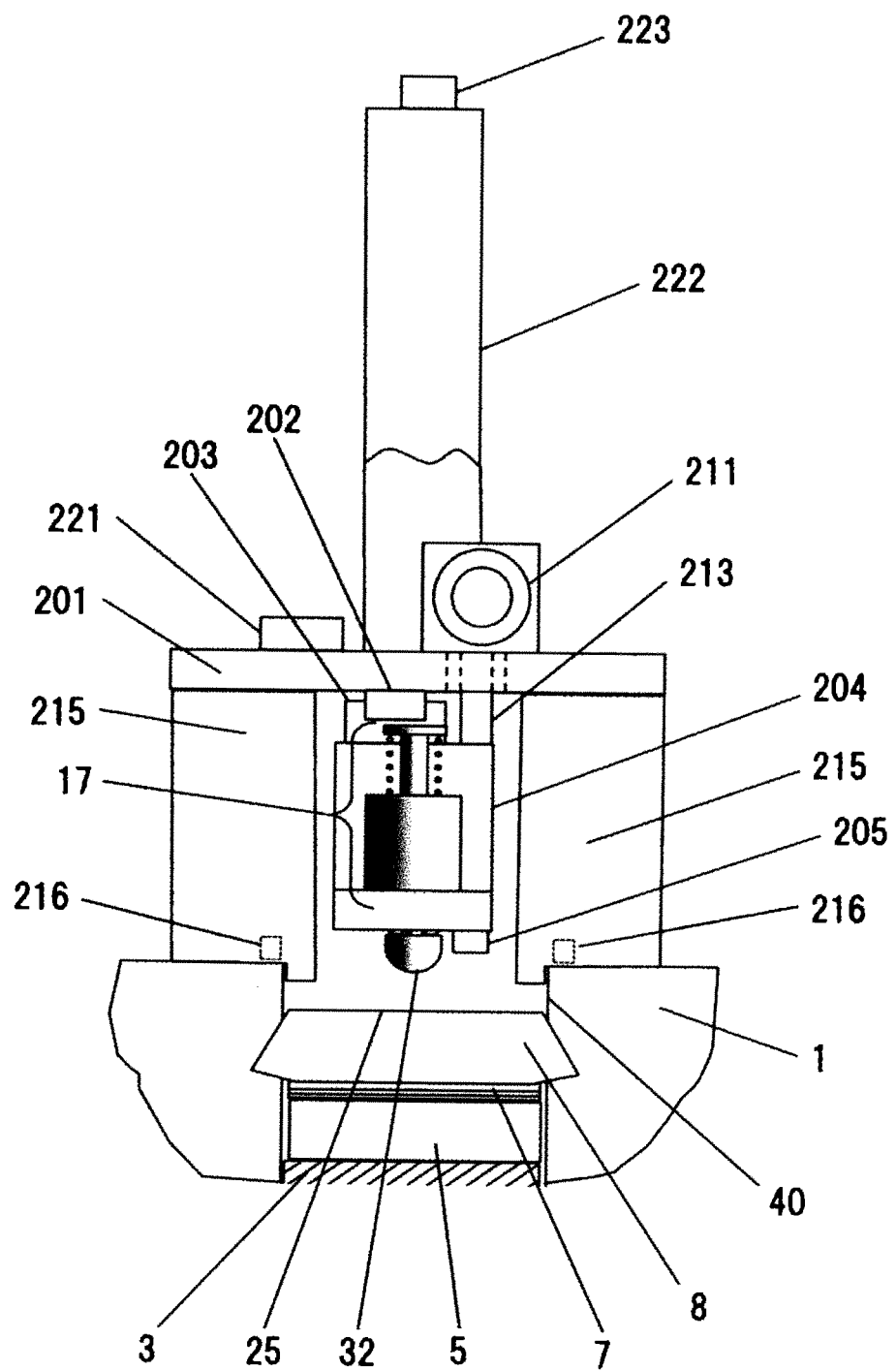
FIG. 16 is a diagram taken along the line F-F in FIG. 15.

FIG. 15 shows a construction of a wedge tightness measuring apparatus of the second embodiment. FIG. 16 is a diagram taken along the line F-F in FIG. 15.

In FIG. 15, reference numeral 200 denotes a measuring probe in the wedge tightness measuring apparatus. In the measuring probe 200, reference numeral 201 denotes a base plate, 202 indicates a guide rail fixed to the base plate 201, and 203 denotes a linear guide fitted to the guide rail. The linear guide 203 is movable along the guide. Reference numeral 204 denotes a bracket fixed to the linear guide 203 and 17 indicates the tapping mechanism fixed to the bracket 204. This tapping mechanism has the same structure as that in the embodiment 1. Reference numeral 205 denotes a microphone fixed to the bracket 204. The microphone collects the tap tone generated when the wedge 8 has been tapped by the tapping mechanism 17.

Reference numeral 208 denotes a ball screw rotatably held by bearing blocks 209 and 210 fixed to the base plate 201; 211 a motor for rotating the ball screw 208; 212 a ball nut which is moved by the rotation of the ball screw 208, and 213 coupling metal fittings for coupling the ball nut 212 and the bracket 204. By the above structure, the ball screw 208 is driven by the motor 211 and the tapping mechanism is moved to an arbitrary position in the longitudinal direction (right/left direction in the diagram) of the wedge 8 and can tap at the arbitrary position.

Reference numeral 215 denotes guide blocks which are fixed to positions near four corners of the base plate 201 and are fitted into a groove 40 of the core 1, thereby deciding the position of the measuring probe. Reference numeral 216 denotes core detecting sensors fixed to the four guide blocks 215, respectively. The sensors 216 detect that the probe 200 has been depressed to the core 1. As such a sensor, a reflection type photoelectric sensor, a proximity sensor using an electromagnetic induction, a small micro switch, or the like can be used. Reference numeral 221 denotes an acceleration sensor fixed to the base plate 201. The sensor 221 detect a gravity acceleration, thereby detecting a posture of the probe 200.

Reference numeral 222 denotes a handle fixed to the base plate 201. A person grasps this handle and depresses the measuring probe 200 to the core. Reference numeral 223 denotes a push-button switch to start the measurement. This switch has been fixed to the handle.

Subsequently, a construction of a control processing unit 250 of the measuring probe 200 will be described.

Since the construction is substantially the same as that of the embodiment 1, only different portions will be described.

In the control processing unit 250, a portion different from that of the embodiment 1 is a portion regarding the control of the motor for moving the tapping mechanism 17. A motor controller 260 for controlling the motor 211 and a motor driver 261 are connected to the MPU 61 and the position of the tapping mechanism 17 is controlled by a command from the MPU 61.

Figure 17:
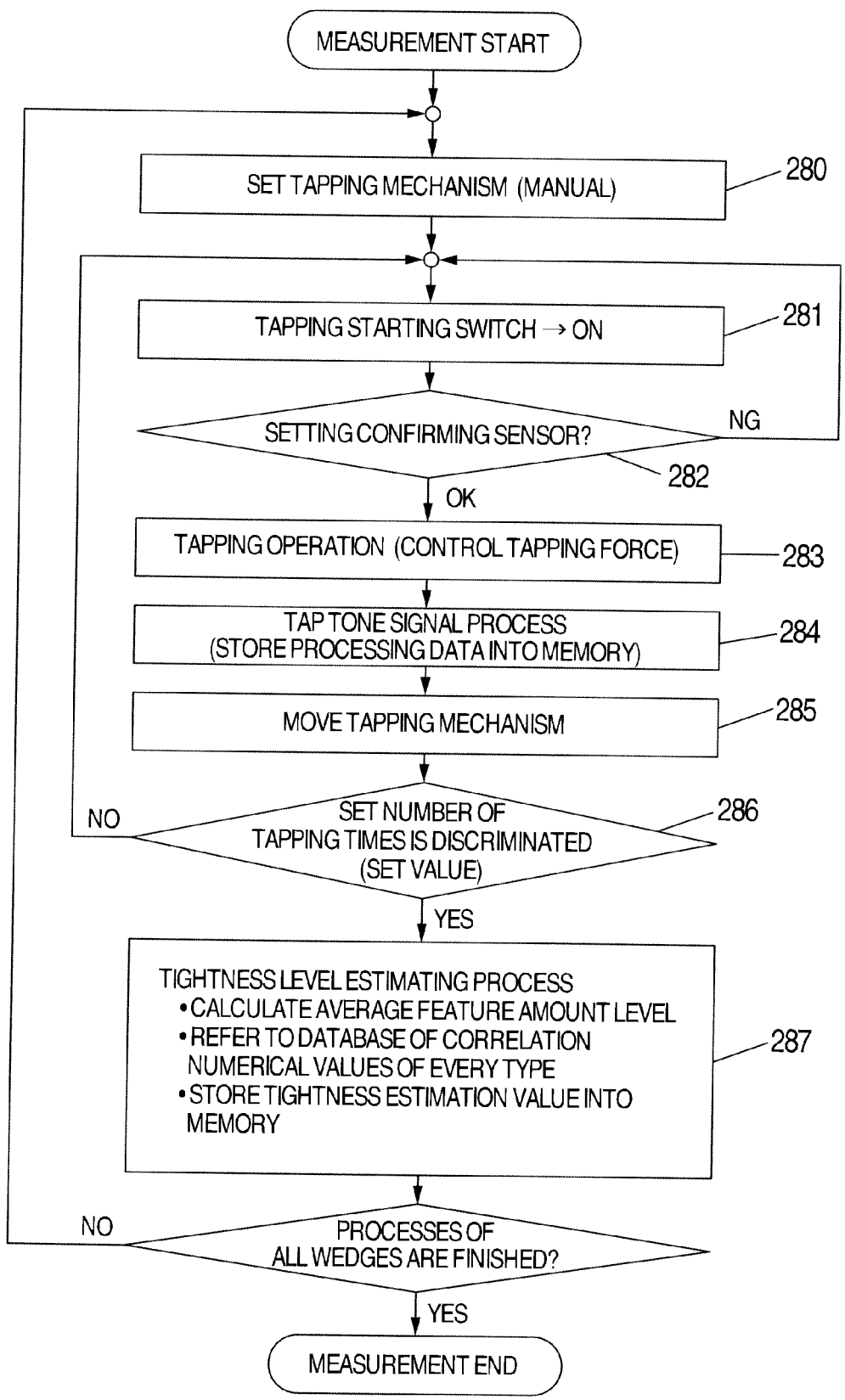
FIG. 17 is a flowchart showing the operation of the embodiment 2.

A tightness measuring method of the embodiment 2 will be described hereinbelow with reference to an operation flow shown in FIG. 17.

First, for the stator core having the measurement target wedge, the guide blocks 215 of the measuring probe 200 are inserted into the groove of the core and the position of the measuring probe 200 is decided as a positioning operation 280.

Subsequently, the measurement starting switch 223 is turned on as a measurement starting operation 281. At this time as a confirmation 282 of the setting of the measuring probe, if all of the core detecting sensors 216 fixed at the four corners are ON, it is determined that the measuring probe 200 has been depressed to the core 1, and the measuring operation is started. The monitoring of the depression state by the core detecting sensors 216 is always performed during the measurement. Only when the four core detecting sensors 216 are ON, the measuring operation is executed.

If the measuring probe has correctly been depressed, a tapping operation 283 to the wedge 8 by the tapping mechanism 17 is started. First, as illustrated in FIG. 15, a position near the left edge of the wedge 8 is tapped by the tapping mechanism 17 and the tap tone at this time is collected by the microphone 205. The tapping operation 283 and a tap tone signal process 284 at this time are similar to those in the embodiment 1. After completion of the tap tone signal process of the first time, a tapping mechanism movement 285 is executed. The motor 211 is controlled by the MPU 61 and the ball screw 208 is driven, thereby moving the tapping mechanism 17 any a predetermined distances. The tapping operation 283 and the tap tone signal process 284 are executed again by the tapping mechanism 17. After that, until the number of tapping times reaches a preset number, the tapping operation and the tap tone signal process are repeated while moving the tapping mechanism, thereby obtaining a plurality of tap tone signal data.

Substantially the same processes as those in the embodiment 1 are executed, total power levels obtained from the plurality of tap tones are averaged and an estimation value of the tightness is obtained and recorded into the memory 74.

In this manner, the tightness estimation value to one wedge is obtained. Subsequently, a similar procedure is repeated, tightness estimation values are obtained with respect to all wedges of the generator stator serving as a measurement target, and the measurement is finished.

A person confirms the wedge tightness data recorded in the memory 74 by using the personal computer 75 and the display 76 such as an LCD connected to the processing unit 250 and stores them as data for management into the external memory 77.

According to the foregoing measuring method, since the wedge 8 is tapped by the tapping force which has properly been controlled, the variation in total power level of the tap tone that is caused by the variation in the tapping force can be reduced. Since the tapping position to the wedge can be controlled, an arbitrary number of tap tones can be collected. Many tap tone samples to obtain the average total power level for one wedge can be obtained. Thus, since the estimation range Δf of the tightness shown in FIG. 12 can be reduced, the estimation precision can be raised.

The invention is not limited to the foregoing embodiments but various modifications are incorporated. For example, the foregoing embodiments are described in detail in order to explain the invention so as to be easily understood and are not always limited to an example having all of the above-described constructions. A part of a certain embodiment can be replaced by the construction of another embodiment or the construction of another embodiment can be also added to the construction of a certain embodiment. An addition, a deletion, or a replacement of another construction can be performed with respect to a part of the construction of each embodiment. Connecting lines of the component elements which are considered to be necessary for description are shown and all of the connecting lines are not always shown in terms of products. Actually, it is possible to consider that most of all of the constructions are mutually connected.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A tightness measuring apparatus of a fixed member, comprising:
tapping means for applying a controlled tapping force to a plurality of positions on a surface of the one member, thereby allowing tap tones to be generated;
tone collecting means for collecting the plurality of generated tap tones;
arithmetic operating means for obtaining one feature amount from the plurality of collected tap tones by an arithmetic operation and obtaining a tightness corresponding to said feature amount by using a database showing a correlation between tightness of said member and a feature amount of the tap tone,
the tapping means having a plurality of hammers for tapping the surface of the one member, a plurality of solenoids each of which drives each of the hammers, and a plurality of springs each of which acts to keep each of the hammers at a predetermined position when no current is supplied to each of the solenoids;
detecting means of a gravity acceleration; and
means for controlling a driving current of said tapping means on the basis of a signal of said gravity acceleration.

2. An apparatus according to claim 1, wherein said member is a ripple member and is fixed by an elastic force of a ripple spring, and said plurality of tapping positions are arranged along a longitudinal direction of said ripple spring.

3. An apparatus according to claim 1, wherein a sum value of power levels at respective frequencies obtained from a power spectrum of the collected tap tones is used as said feature amount.

4. An apparatus according to claim 1, wherein a sum value of amplitude levels at respective frequencies obtained from an amplitude spectrum of the collected tap tones is used as said feature amount.

5. An apparatus according to claim 1, wherein an attenuation factor of a vibration waveform of an intensity level of the collected tap tones is used as said feature amount.

6. An apparatus according to claim 1, wherein in power spectrum distribution of the collected tap tones, a value of a frequency at which a sum value of power levels at respective frequencies is divided into the halves at the upper and lower frequency bands is used as said feature amount.

7. An apparatus according to claim 1, wherein in amplitude spectrum distribution of the collected tap tones, a value of a frequency at which a sum value of amplitude levels at respective frequencies is divided into the halves at the upper and lower frequency bands is used as said feature amount.

8. An apparatus according to claim 1, wherein said tapping means controls the tapping force by a PWM (Pulse Width Modulation) system by using a solenoid type actuator.

9. An apparatus according to claim 8, wherein said tapping means independently controls a plurality of hammers to each solenoid by using a plurality of actuators.

10. An apparatus according to claim 1, wherein said tapping means has moving means which can control positions of an actuator and a hammer, the positions of the actuator and the hammer are changed by said moving means, and a tapping is performed a plurality of number of times.

11. An apparatus according to claim 1, wherein said tone collecting means collects a tap tone signal from a microphone only for a predetermined time by using a tapping start signal of said tapping means as a reference.

12. An apparatus according to claim 1, further comprising means for detecting a positional relation between said member as a measurement target and the tightness measuring apparatus.

13. An apparatus according to claim 1, further comprising:
input means for receiving an input of material information and shape information regarding the target member in the case where information regarding said member as a measurement target does not exist in a database; and
means for calculating an approximate function showing a correlation between the tightness of said member as a measurement target and the feature amount from data which has been inputted to the information database on the basis of data of a material and a shape which are closest to those of the target member into which said material information and said shape information have been inputted.

14. An apparatus according to claim 1, further comprising:
input means for receiving an input of material information and shape information regarding the member in the case where information regarding said member as a measurement target does not exist in a database; and
a processing unit for representing a database of the member whose physical properties or shape are closest from the information of the member which has previously been obtained and receiving a selection.

15. A tightness measuring apparatus of a fixed member, comprising:
tapping means for applying a predetermined controlled tapping force to a plurality of positions on a surface of the one member, thereby allowing a plurality of tap tones to be generated;
tone collecting means for collecting the plurality of generated tap tones;
arithmetic operating means for obtaining a plurality of first feature amounts from the plurality of collected tap tones, obtaining one second feature amount from the plurality of first feature amounts by an arithmetic operation, and obtaining a tightness in correspondence to a tightness corresponding to said second feature amount by using a database showing a correlation between tightness of said member and said second feature amount of the tap tone,
the tapping means having a plurality of hammers for tapping the surface of the one member, a plurality of solenoids each of which drives each of the hammers, and a plurality of springs each of which acts to keep each of the hammers at a predetermined position when no current is supplied to each of the solenoids;
detecting means of a gravity acceleration; and
means for controlling a driving current of said tapping means on the basis of a signal of said gravity acceleration.

16. An apparatus according to claim 15, wherein in an arithmetic operating method of obtaining the one second feature amount from the plurality of first feature amounts by the arithmetic operation, an average value of said plurality of first feature amounts is set to said second feature amount.

17. A tightness measuring method of a fixed member, comprising the steps of:
applying a controlled tapping force to a plurality of positions on a surface of the one member by using tapping means having a plurality of hammers for tapping the surface of the one member, a plurality of solenoids each of which drives each of the hammers, and a plurality of springs each of which acts to keep each of the hammers at a predetermined position when no current is supplied to each of the solenoids, thereby allowing tap tones to be generated, and collecting the plurality of generated tap tones;
obtaining one feature amount from the plurality of collected tap tones by an arithmetic operation and estimating tightness corresponding to said feature amount by using a correlation between tightness of said member and feature amount which has previously been obtained;
detecting a gravity acceleration; and
controlling a driving current of said tapping means on the basis of a signal of said gravity acceleration.

18. A tightness measuring method of a fixed member, comprising the steps of:
applying a predetermined controlled tapping force to a plurality of positions on a surface of the one member by using tapping means having a plurality of hammers for tapping the surface of the one member, a plurality of solenoids each of which drives each of the hammers, and a plurality of springs each of which acts to keep each of the hammers at a predetermined position when no current is supplied to each of the solenoids, thereby allowing a plurality of tap tones to be generated, and collecting the plurality of generated tap tones;
obtaining one second feature amount by an arithmetic operation from a plurality of first feature amounts obtained from the plurality of tap tones and obtaining a tightness of the member in correspondence to a tightness corresponding to said second feature amount by using a correlation between the tightness of the member and the second feature amount which has previously been obtained;
detecting a gravity acceleration; and
controlling a driving current of said tapping means on the basis of a signal of said gravity acceleration.

19. A method according to claim 18, wherein in an arithmetic operating method of obtaining the one second feature amount from the plurality of first feature amounts by the arithmetic operation, an average value of said plurality of first feature amounts is set to said second feature amount.

* * * * *